United States Patent
Yue

(10) Patent No.: US 10,894,051 B2
(45) Date of Patent: Jan. 19, 2021

(54) METHOD OF TREATING METASTATIC CANCER IN A SUBJECT

(71) Applicant: City University of Hong Kong, Kowloon (HK)

(72) Inventor: Jianbo Yue, Kowloon Tong (HK)

(73) Assignee: City University of Hong Kong, Kowloon (HK)

( * ) Notice: Subject to any disclaimer, the term of this patent is extended or adjusted under 35 U.S.C. 154(b) by 0 days.

(21) Appl. No.: 15/609,184

(22) Filed: May 31, 2017

(65) Prior Publication Data
US 2018/0344744 A1    Dec. 6, 2018

(51) Int. Cl.
*A61K 31/5377*    (2006.01)
*A61K 45/06*    (2006.01)
*A61K 9/00*    (2006.01)

(52) U.S. Cl.
CPC ........ *A61K 31/5377* (2013.01); *A61K 9/0019* (2013.01); *A61K 9/0053* (2013.01); *A61K 45/06* (2013.01)

(58) Field of Classification Search
CPC .............. A61K 31/5377; A61K 9/0053; A61K 9/0019; A61K 45/06; A61P 35/04
See application file for complete search history.

(56) References Cited

U.S. PATENT DOCUMENTS

2008/0131434 A1*  6/2008  Lewicki ................ C07K 16/28
                                                       424/138.1

FOREIGN PATENT DOCUMENTS

WO    WO-2015085229 A1 *  6/2015   ........... A61K 31/473
WO    WO 2015124120 A1 *  8/2015   ......... A61K 31/5377

* cited by examiner

*Primary Examiner* — Sarah Pihonak
(74) *Attorney, Agent, or Firm* — Renner Kenner Greive Bobak Taylor & Weber

(57) ABSTRACT

A method of treating metastatic cancer in a subject suffering from metastatic cancer includes administering an effective amount of a compound having a structure of Formula I, in particular a compound having a structure of Formula II, to the subject. Also, a method of inhibiting metastasis of cancer cells includes contacting the cancer cells with an effective amount of a compound having the structure of Formula I, in particular a compound having the structure of Formula II.

5 Claims, 14 Drawing Sheets

LCSCs

METHOD OF TREATING METASTATIC CANCER IN A SUBJECT

TECHNICAL FIELD

The present application relates to a method of treating metastatic cancer in a subject, in particular but not exclusively includes a step of administering a small chemical compound to the subject in particular a mammal. The present application also relates to a method of inhibiting metastasis of cancer cells.

BACKGROUND OF THE INVENTION

Metastasis of cancer refers to a spread of cancer cells from one part of the body to nearby tissues, organs or even distant parts of the body. Some cancer cells may have the ability to penetrate the blood vessels and lymphatic vessels and therefore travel around the body via the blood circulation and lymphatic system. Once the cancer cells metastasize, new tumors are usually found on a second site of the body and this is called metastatic cancer. For example, but not limiting, common sites where cancer spreads are the bone, liver, and lung.

Once cancer cells metastasize, it can be hard to control. Metastasis remains as the major cause of mortality accounting for about 90% of total cancer deaths. Although there are methods to treat some types of metastatic cancer, most of the currently available methods are found to be not as effective as desired. In particular, there is currently no drug on the market that can effectively treat or inhibit metastasis of cancers.

As treatment options for metastatic cancer are limited, there remains a strong need for novel compounds which are effective against metastasis of cancer and in the treatment of metastatic cancer.

SUMMARY OF THE INVENTION

The inventor found that a small chemical compound vacuolin-1 has an anti-metastatic effect against cancer cells, in particular can compromise the disassembly dynamic of focal adhesion so as to suppress the invasion of various tumor cells in vitro. The experimental results also prove that the use of vacuolin-1 in pretreating cancer cells can significantly inhibit the tumor-seeding ability of tumor cells in xenograft mouse. Moreover, vacuolin-1 is found to be effective in inhibiting the metastasis of human lung cancer cells and human breast cancer cells in xenograft mouse models. Further, it is also found that vacuolin-1 does not possess obvious acute, sub-acute and sub-chronic toxicity in mice. Accordingly, it is believed that the compound of the present invention is effective against metastasis of cancer, and be applied in a treatment of metastatic cancer.

In a first aspect, the present invention provides a method of treating metastatic cancer in a subject suffering from metastatic cancer, comprising the step of administering an effective amount of a compound having a structure of Formula I to the subject,

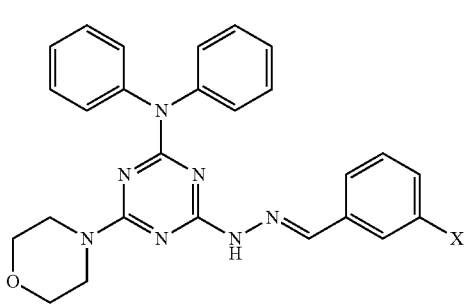

Formula I wherein X is a hydrogen, hydroxyl, or halogen.

In an embodiment, the compound has a structure of Formula I with X being a halogen. In particular, the compound has a structure of Formula II,

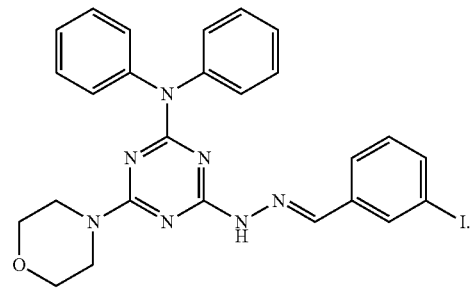

Formula II

In embodiments, the metastatic cancer is selected from the group consisting of bladder cancer, breast cancer, colon cancer, kidney cancer, lung cancer, ovary cancer, skin cancer, pancreatic cancer, prostate cancer, liver cancer and bone cancer. Preferably, the metastatic cancer is breast cancer, liver cancer or lung cancer.

In an embodiment, the compound is administered to the subject by a route selected from a group consisting of oral delivery, intravenous delivery, intradermal delivery, intraperitoneal delivery and intramuscular delivery.

In an advanced embodiment, the compound is administered in combination with one or more chemotherapy or immunotherapy drug to the subject. Preferably, the chemotherapy drug may be selected from the group consisting of taxol, 5-Fu, and temirolimus, and immunotherapy drug may be programmed cell death protein 1 (PD-1) or a programmed death-ligand 1 (PD-L1) inhibitor.

In a second aspect, the present invention also pertains to a method of inhibiting metastasis of cancer cells, comprising the step of contacting the cancer cells with an effective amount of a compound having the structure of Formula I

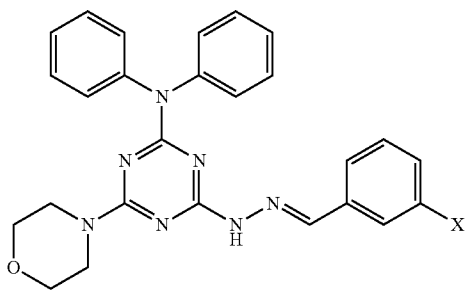

Formula I wherein X is hydrogen, hydroxyl, or halogen.

Preferably, the compound has the structure of Formula II as described above,

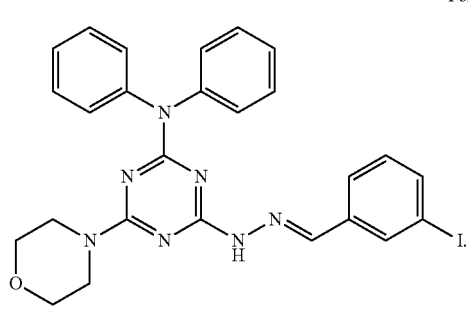

Formula II

In particular, the compound is contacted with the cancer cells at a concentration of about 2 μM or above.

Those skilled in the art will appreciate that the invention described herein is susceptible to variations and modifications other than those specifically described. The invention includes all such variations and modifications. The invention also includes all steps and features referred to or indicated in the specification, individually or collectively, and any and all combinations of the steps or features.

Other features and aspects of the invention will become apparent by consideration of the following detailed description and accompanying drawings.

DETAILED DESCRIPTION OF THE EMBODIMENTS

Figure 1A:
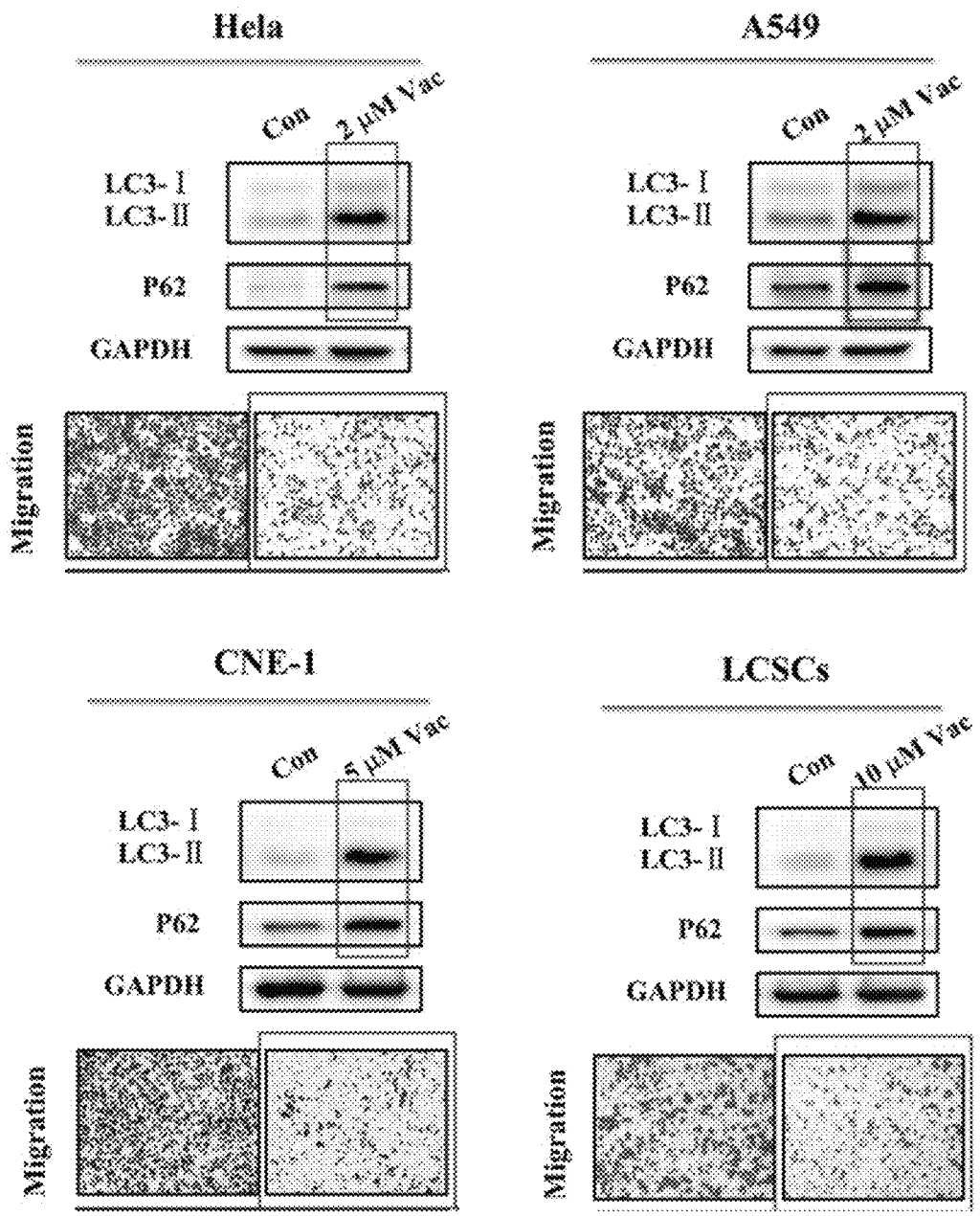
FIG. 1A shows the effects of vacuolin-1 on migration of cancer cells, namely HeLa cells, A549 cells, CNE-1 cells and human liver cancer stem cells (hLCSCs) which were treated with vacuolin-1 at different concentrations (2 μM, 5 μM and 10 μM).

Unless otherwise defined, all technical terms used herein have the same meaning as commonly understood by one skilled in the art to which the invention belongs.

As used herein, "comprising" means including the following elements but not excluding others. "Essentially consisting of" means that the material consists of the respective element along with usually and unavoidable impurities such as side products and components usually resulting from the respective preparation or method for obtaining the material such as traces of further components or solvents. "Consisting of" means that the material solely consists of, i.e. is formed by the respective element. As used herein, the forms "a," "an," and "the," are intended to include the singular and plural forms unless the context clearly indicates otherwise.

The present invention in the first aspect provides a method of treating metastatic cancer in a subject suffering from metastatic cancer, comprising the step of administering an effective amount of a compound having a structure of Formula I to the subject, Formula I

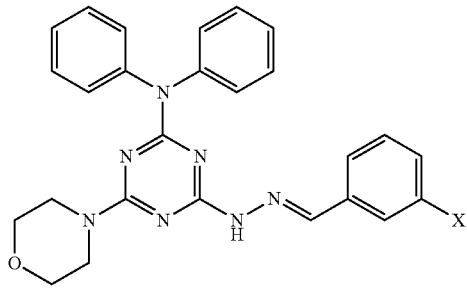

wherein X is a hydrogen, hydroxyl, or halogen.

The metastatic cancer as used herein refers to cancer cells having the ability to spread from one site in the body of a subject to a second site in the body of a subject, in particular to a non-adjacent part of the body. The cancer may be selected from the group consisting of bladder cancer, breast cancer, colon cancer, kidney cancer, lung cancer, ovary cancer, skin cancer, pancreatic cancer, prostate cancer, liver cancer and bone cancer.

In a preferred embodiment, the cancer is breast cancer, liver cancer or lung cancer.

"Treating" the metastatic cancer in particular includes inhibiting the migration of cancer cells, suppressing the invasion of cancer cells to other tissues, inhibiting the formation of metastatic cancer cells at a secondary site, suppressing the disassembly dynamic of focal adhesion in the cancer cells, and/or alleviating one or more symptoms of the metastatic cancer. In particular the term treating includes inhibiting the migration of cancer cells, suppressing the invasion of cancer cells to other tissues, or inhibiting the formation of metastatic cancer cells at a secondary site.

The expression "effective amount" generally denotes an amount sufficient to produce therapeutically desirable results, wherein the exact nature of the result varies depending on the specific condition which is treated. The compound of the present invention may be contained in a composition, in particular the pharmaceutical composition, in an effective amount, i.e. an amount suitable to treat or prevent the metastatic cancer or inhibit the metastasis of cancer cells in a subject, in particular a mammal, which also depends on the frequency and number of compositions to be administered. In an embodiment, the compound of the present invention may be administered to a subject at a concentration of about 2 µM or 2.5 mg/kg or above. In other embodiment, the compound may be administered at a concentration of about 2.5 mg/kg, 5 mg/kg, 8 mg/kg or 10 mg/kg.

The term "subject" in particular refers to an animal or a human, in particular a mammal and most preferably a human. I.e. the subject is in most preferred embodiments a human suffering from a cancer or a metastatic cancer. The subject may also be a cancer patient as risk for metastasis.

When the compound is provided in a pharmaceutical composition to a subject, the skilled person is able to select suitable pharmaceutically tolerable excipients depending on the form of the pharmaceutical composition and is aware of methods for manufacturing pharmaceutical compositions as well as able to select a suitable method for preparing the pharmaceutical composition depending on the kind of pharmaceutically tolerable excipients and the form of the pharmaceutical composition.

In an embodiment, the compound of the present invention is particular used in combination with one or more chemotherapy or immunotherapy drugs. Preferably, the chemotherapy drug may be selected from the group consisting of taxol, 5-Fu, and temirolimus, and immunotherapy drug may be programmed cell death protein 1 (PD-1) or a programmed death-ligand 1 (PD-L1) inhibitor. The person skilled in the art is able to include other therapeutic compounds which are useful to alleviate the conditions of the subject.

Turning to the compound of the present invention, the compound of Formula I is a small chemical compound which possesses anti-metastatic effects against cancer cells. It is believed that the compound as disclosed herein is capable of inhibiting the migration and/or invasion of cancer cells and thus prevents or inhibits the metastasis of the cancer cells.

The compound has the structure of Formula I

Formula I

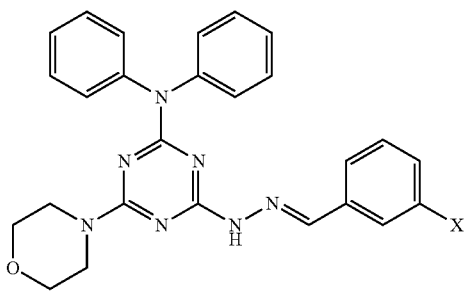

wherein X is a hydrogen, hydroxyl, or halogen. Preferably, the halogen may be selected from I, Br, Cl, or F, in particular from I.

In an embodiment, the compound has the structure of Formula II, also called as vacuolin-1, Formula II

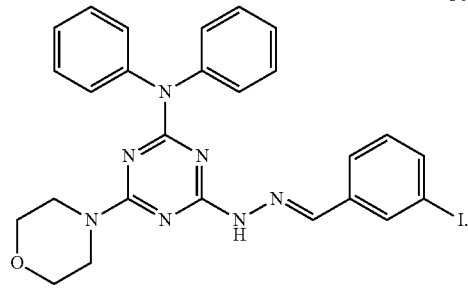

In embodiments of the present invention, the compound as disclosed herein is administered to the subject by a route selected from a group consisting of oral delivery, intravenous delivery, intradermal delivery, intraperitoneal delivery and intramuscular delivery. In particular, the compound is administered to a subject via intraperitoneal delivery. The person skilled in the art is able to formulate the compound in a pharmaceutical composition according to the target site in the body of the subject.

The present invention further provides a method of inhibiting metastasis of cancer cells, comprising the step of contacting the cancer cells with an effective amount of a compound having the structure of Formula I Formula I

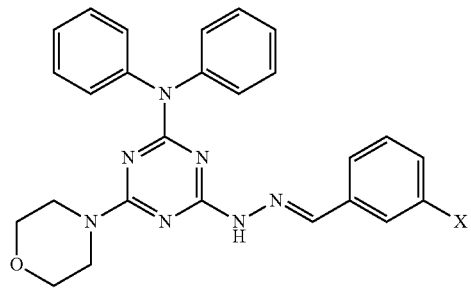

wherein X is hydrogen, hydroxyl, or halogen.

In particular, the compound may have a structure of Formula I with X being a halogen. Preferably, the compound has the structure of Formula II Formula II

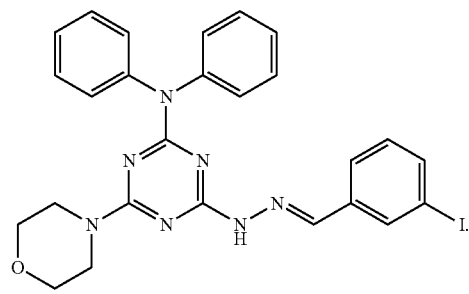

The compound may be contacted with the cancer cells in combination with one or more chemotherapy or immunotherapy drug. The chemotherapy drug may be selected from the group consisting of taxol, 5-Fu, and temirolimus. The immunotherapy drug may be PD-1 or a PD-L1 inhibitor. As described above, the person skilled in the art is able to select suitable chemotherapy or immunotherapy drug according to the types of cancer cells.

The cancer cells may be bladder cancer cells, breast cancer cells, colon cancer cells, kidney cancer cells, lung cancer cells, ovary cancer cells, skin cancer cells, pancreatic cancer cells, prostate cancer cells, liver cancer cells and bone cancer cells. In particular embodiments, the cancer cells are breast cancer cells, liver cancer cells, lung cancer cells or a combination thereof.

In embodiments, the compound is contacted with the cancer cells at a concentration of about 2 µM or above, in particular at a concentration of about 2 µM, about 5 µM, about 8 µM, or about 10 µM. In a particular embodiment, the compound is contacted with the cancer cells at a concentration of 2 µM.

It is believed that the compound as disclosed in the present invention is capable of treating metastatic cancer, and/or inhibiting the migration and invasion of cancer cells. Accordingly, the present invention also pertains to a method of preventing metastasis in a cancer patient at risk for metastasis. In particular, the method includes a step of administering an effective amount of the compound having a structure of Formula I to the patient, which step is as described above.

The experiments as described below further support the anti-metastatic effect of vacuolin-1.

EXAMPLES

Example 1

Effects of Vacuolin-1 on Migration and Invasion of Cancer Cells

Figure 1B:
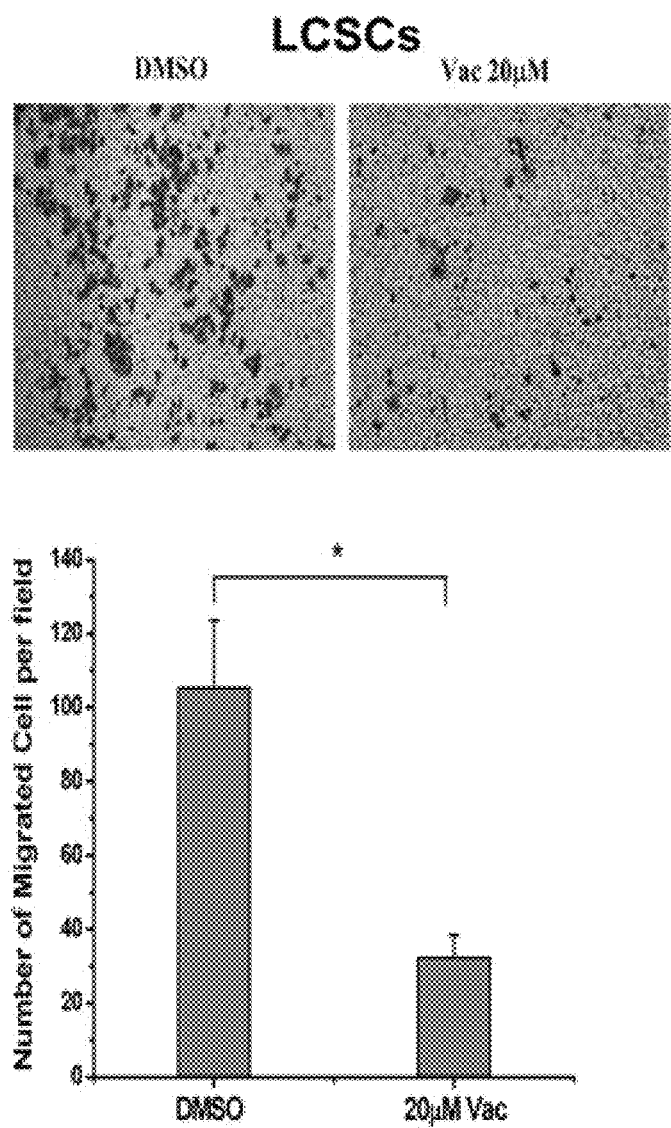
FIG. 1B shows the results obtained from the matrigel invasion assay of vacuolin-1 on hLCSCs.

HeLa cells, A549 cells, CNE-1 cells and human liver cancer stem cells (hLCSCs) were incubated and treated with vacuolin-1 at different concentrations, namely 2 µM, 5 µM and 10 µM. With reference to FIG. 1A, vacuolin-1 dramatically reduced the size and number of colonies generated from single cancer cell. Vacuolin-1 significantly inhibited the cell migration and invasion of HeLa cells, A549 cells, CNE-1 cells and hLCSCs as shown by the trans-well migration assay and matrigel invasion assays in FIGS. 1A and 1B, respectively and is believed to correlate to its effect on autophagy inhibition as shown in the protein assay of LC3-1 and LC3-II.

Figure 1C:
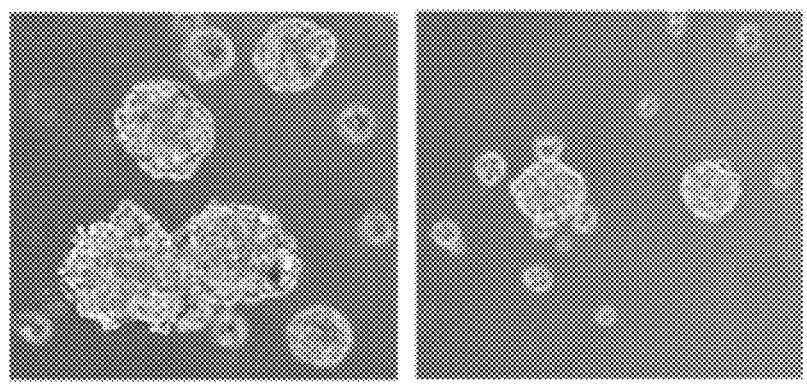
FIG. 1C shows the effects of vacuolin-1 on tumor sphere formation of hLCSCs.
Figure 1C:
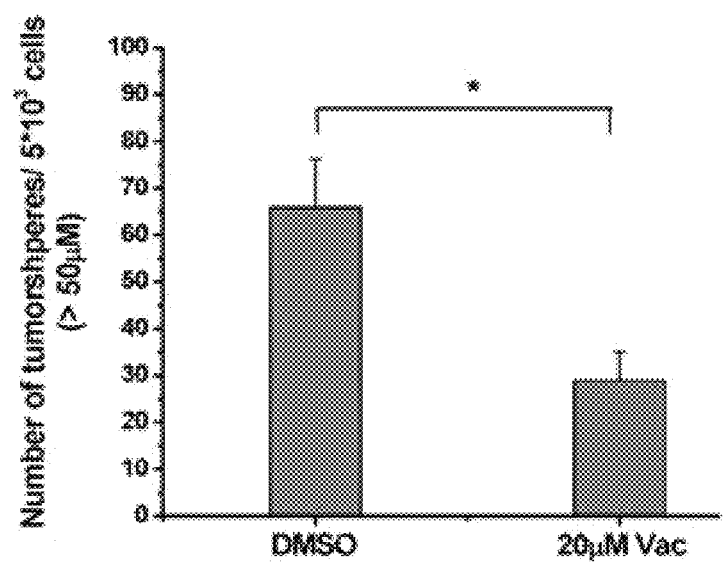

Moreover, as shown in FIG. 1C, vacuolin-1 significantly inhibited tumor sphere formation of hLCSCs. These data suggest that vacuolin-1 is an efficient anti-tumor agent in vitro.

Example 2

Effects of Vacuolin-1 on Spatio-Temporal Regulation of FA Dynamics

Autophagy or endosomal trafficking contributes to the migration and invasion of tumor cells by changing the microtubule dynamics, or presentation of surface proteins, or secretion of extracellular matrix (ECM) proteins. Also, focal adhesion (FA) dynamics is a key process for cell migration. In this regard, the effects of vacuolin-1 on the spatio-temporal regulation of FA dynamics were assessed. Phospho-Y397 FAK immunoblot was used to assess the effects of vacuolin-1 on phosphorylation and dephosphorylation dynamics of FAK. Cells were also treated with nocodazole, followed by nocodazole removal and vacuolin-1 incubation, stained with antibodies against Vinculin and Phalloidiin for FA and stress fiber, respectively.

Figure 1D:
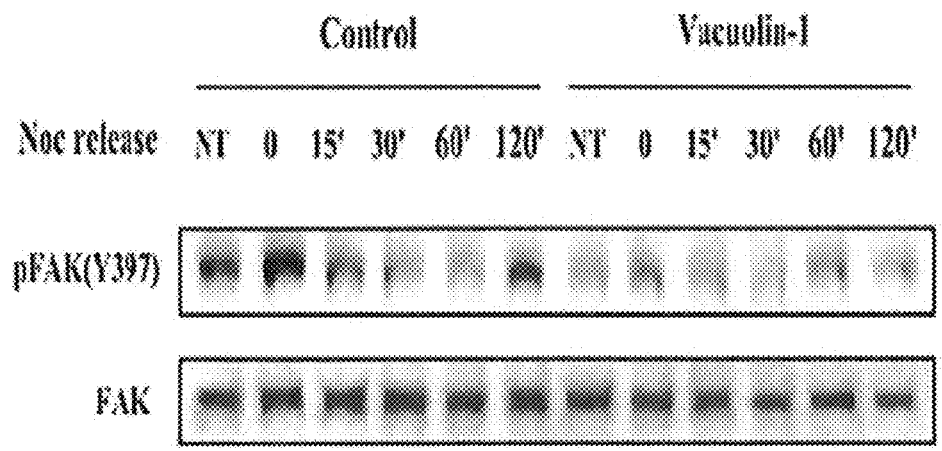
FIG. 1D is a plot obtained from phosphor-Y397 FAK immunoblot analysis and shows the relative amount of pFAK(Y397) and FAK in the cells treated with Vacuolin-1.
Figure 1E:
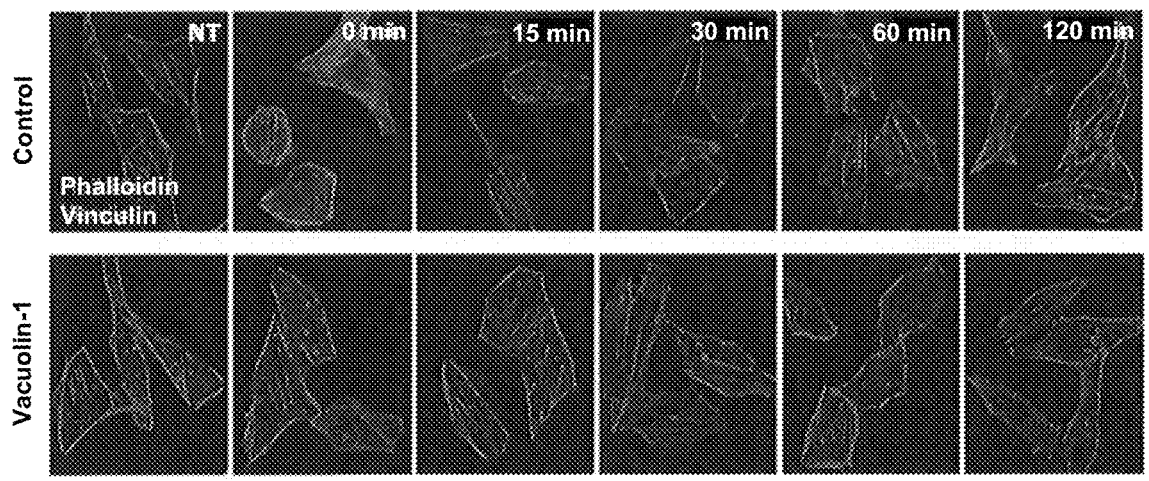
FIG. 1E shows microscopic fluorescence images of cells subjected to nocodazole treatment at different time slots.
Figure 1F:
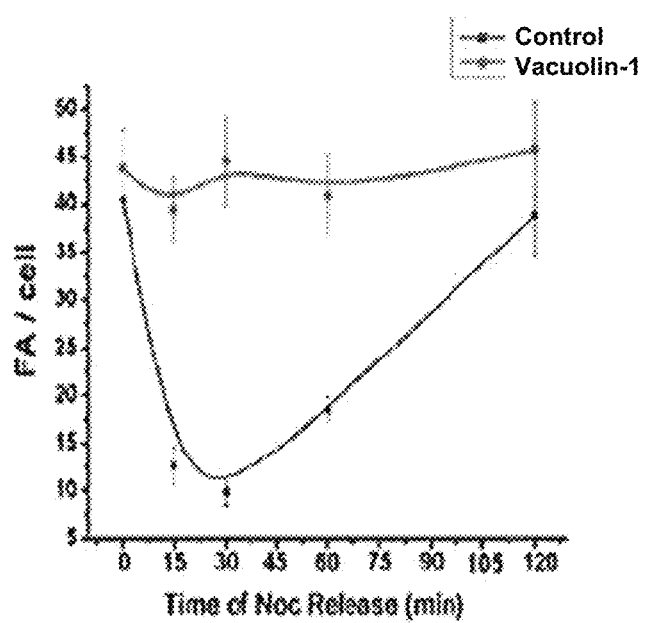
FIG. 1F shows a plot comparing the release of nocodazole in vacuolin-1 treated cells with the control group.

With reference to FIGS. 1E and 1F, cells were treated with nocodazole so as to depolymerize microtubules for inducing and stabilizing FA formation, showing by the puncta staining pattern of Vinculin (green colour), whereas removal of nocodazole led to microtubule regrowth resulting in decreasing the number of FA in a time-dependent manner until the reformation of FAs. Referring to FIGS. 1E and 1F, vacuolin-1 treatment of cells markedly inhibited the FA disassembly, showing by the consistent Vinculin puncta staining after nocodazole released. Focal adhesion kinase (FAK) phosphorylation and dephosphorylation on Y397 is another readout of FA dynamics.

Consistently, with reference to FIG. 1D, vacuolin-1 treatment of cells abolished phosphorylation and dephosphorylation dynamics of FAK as assessed by the phosphor-Y397

FAK immunoblot analysis. Accordingly, these data indicate that vacuolin-1 compromises the disassembly dynamic of FA to suppress the migration/invasion of tumor cells.

Example 3

Effects of Vacuolin-1 Pretreatment on Cancer Cells

Figure 2A:
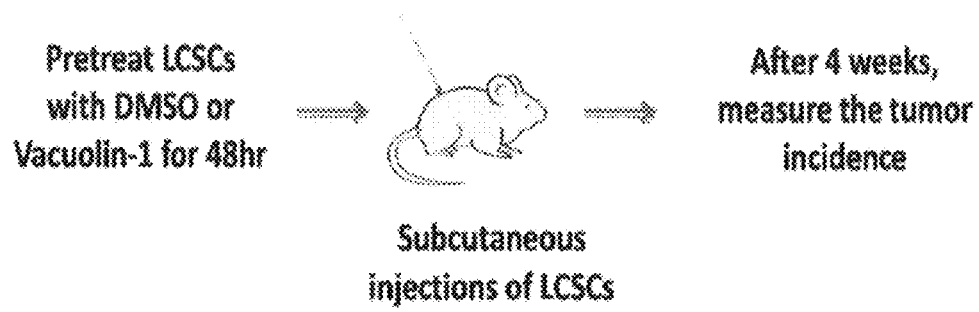
FIG. 2A is a schematic diagram showing a method for testing the in vivo effect of vacuolin-1 pretreatment on cancer cells, i.e. hLCSCs, in nude mice so as to determine whether vacuolin-1 possesses inhibitory activity on cancer cell invasion.

Since vacuolin-1 exhibits no cytotoxicity but markedly inhibits invasion of cancer cells in vitro, the ability of vacuolin-1 on pre-treatment was tested on xenograft tumor-seeding. Nude mice were divided into 4 control groups and 4 treatment groups, each group having 6 nude mice. With reference to FIG. 2A, LCSCs were pretreated with DMSO or 10 µM vacuolin-1 for 48 hours before injecting to nude mice via subcutaneous injection. After 4 weeks, the tumor incidence in mice was measured to determine whether the pretreatment of vacuolin-1 can inhibit the invasion cancer cells in mice.

Table 1 below shows the results measured after 4 weeks of treatment.

| Cell number | LCSCs injected subcutaneously | | | |
| --- | --- | --- | --- | --- |
| (cells) | $1*10^3$ | $1*10^4$ | $1*10^5$ | $1*10^6$ |
| Control | 1/6 (479 mm$^3$) | 3/6 (1897 mm$^3$) | 4/6 (2061 mm$^3$) | 6/6 (3065 mm$^3$) |
| Vacuolin-1 | 0/6 | 2/6 (1069 mm$^3$) | 2/6 (1184 mm$^3$) | 5/6 (1521 mm$^3$) |

Figure 2B:
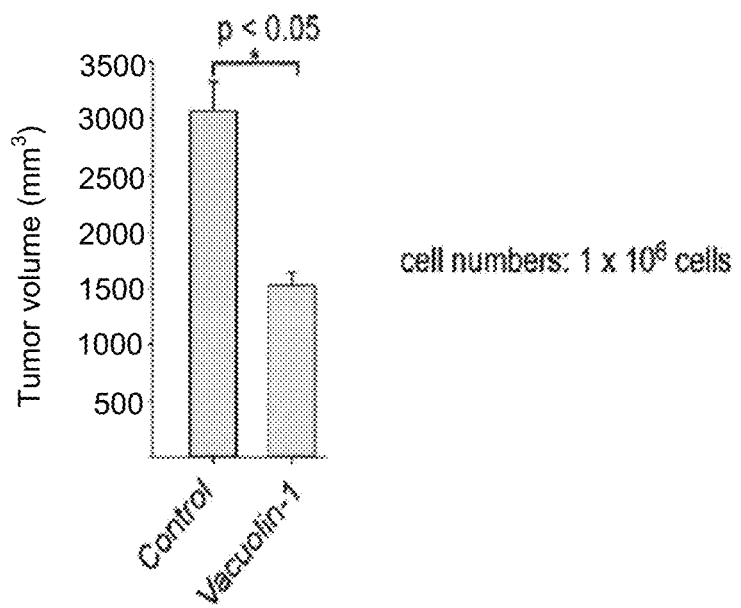
FIG. 2B is a plot of tumor volume measured against control group having LCSCs pretreated with DMSO and treatment group having LCSCs pretreated with vacuolin-1 wherein treatment group shows a marked decrease in tumor volume.

Based on the above results and FIG. 2B, vacuolin-1 pretreatment on human LCSCs markedly inhibited tumor-seeding ability of LCSC cells in nude mice. Statistical analysis on the cell seeding concentration of $1\times10^6$ cells was performed, p<0.05.

Example 4

Anti-Metastasis Effect of Vacuolin-1 on Cancer Cells

The most damaging change during tumor progression is the switch from a locally growing tumor to a metastatic killer. Since vacuolin-1 markedly inhibited the migration of both cancer stem cells and carcinoma cells, the inventor tested the ability of vacuolin-1 on suppressing the metastasis of xenograft tumor in nude mice.

Figure 3A:
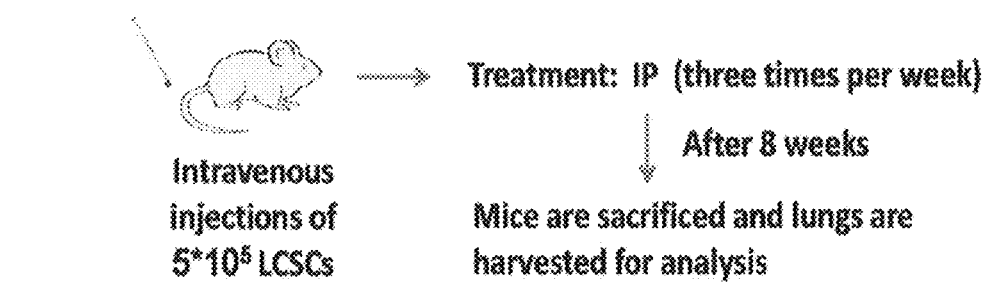
FIG. 3A is a schematic diagram showing a method for testing the in vivo effects vacuolin-1 on metastasis of hLCSCs in nude mice so as to determine whether vacuolin-1 possesses anti-metastasis activity.

With reference to FIG. 3A, briefly, $5\times10^5$ tfLC3B-expressing LCSCs were injected via tail vein into nude mice. 24 hours after the tail vein injection, intraperitoneal (IP) injection of vacuolin-1 (2.5 mg/kg) were conducted 3 times per week. After 8 weeks, all mice were sacrificed. Lungs were excised, and fixed in the 4% paraformaldehyde in PBS. Metastatic nodules were counted in the excised lungs and hemotoxylin/eosin (H&E) were then performed.

Figure 3B:
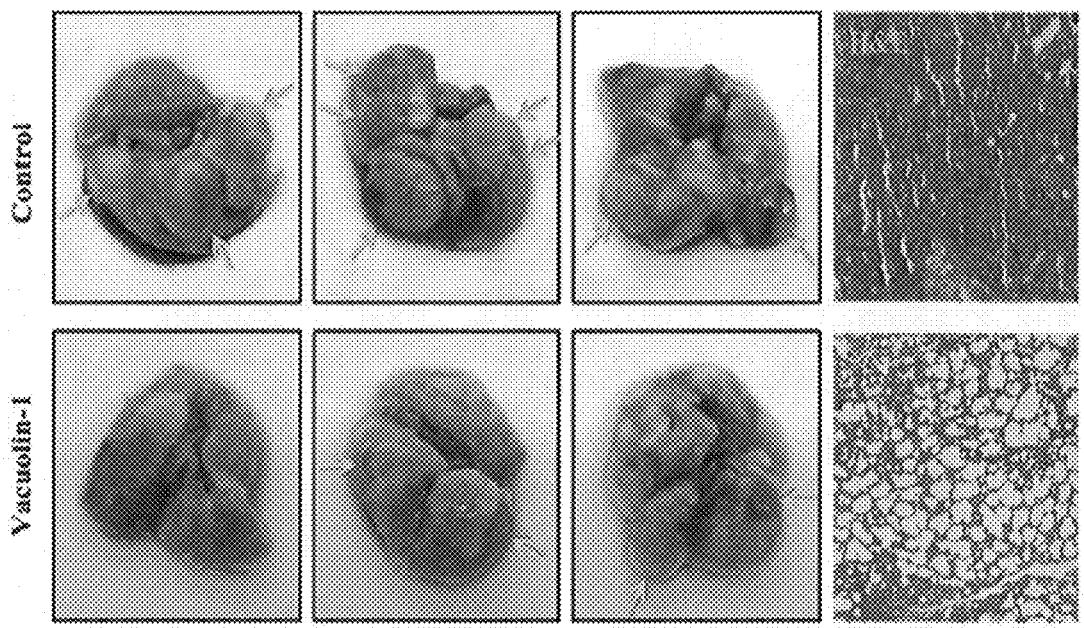
FIG. 3B shows photographs and microscopic images of the excised lungs after treatment of vacuolin-1 and compared with the control group.
Figure 3C:
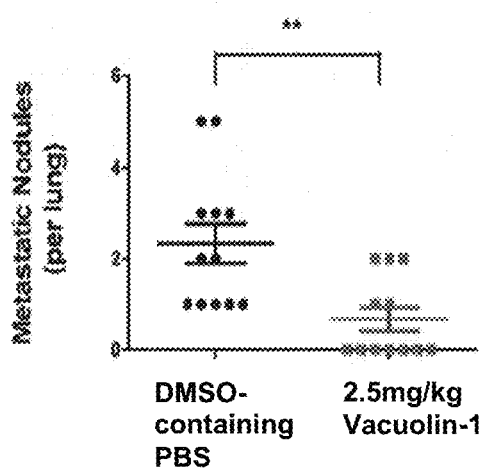
FIG. 3C is a plot showing the number of metastatic nodules found in the excised lungs for both the control group and treatment group.

With reference to FIGS. 3B and 3C, vaculin-1 treatment significantly inhibited the metastasis of LSCSs, manifested by the much less numbers of tumor nodules in lung and normal lung histology in vacuolin-1 treated groups as compared to control groups.

Figure 4A:
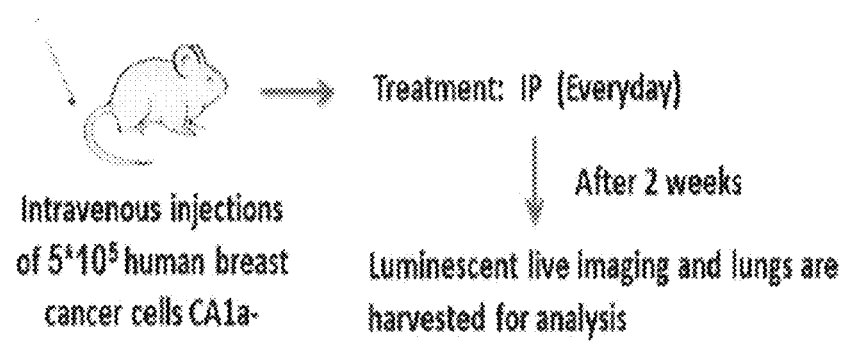
FIG. 4A is a schematic diagram showing a method for testing the in vivo effects vacuolin-1 on metastasis of human breast cancer cells in nude mice so as to determine whether vacuolin-1 possesses anti-metastasis activity.

Similarly, the anti-metastasis effects of vacuolin-1 in human breast cancer cells CA1a in xenograft mouse models were evaluated. With reference to FIG. 4A, briefly, $5\times10^5$ Fluc-mCherry-expressing CA1a cells were injected by tail vein into nude mice. 24 hours after the tail vein injection, IP injections of vacuolin-1 (2.5 mg/kg) and DMSO-containing PBS were conducted 3 times per week. The mice where imaged by the Cri Maestro 2 weekly to assess the tumor progression. After 8 weeks, all mice were sacrificed.

Figure 4B:
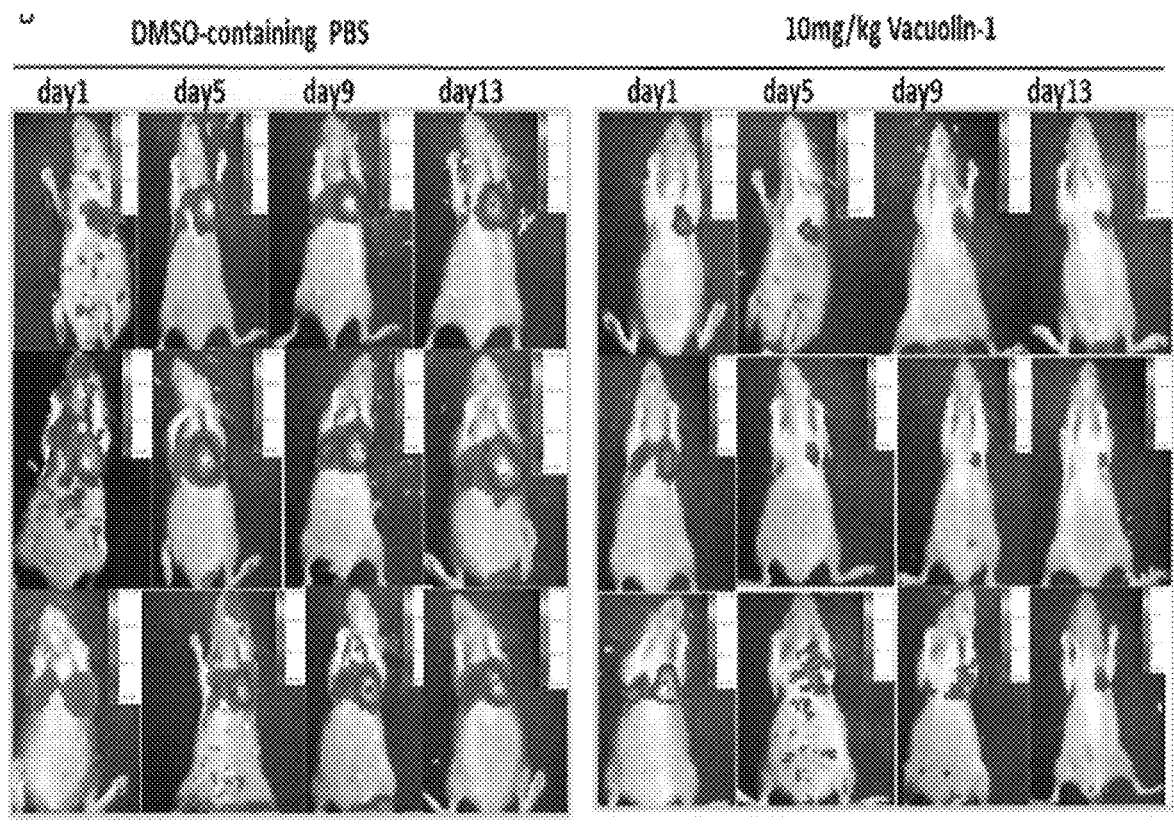
FIG. 4B shows images of the mice obtained by Cri Maestro 2 after treatment of vacuolin-1 and compared with the control group.

As shown in FIG. 4B, vacuolin-1 treatment significantly inhibited the metastasis of human breast cancer cells CA1a.

Figure 5A:
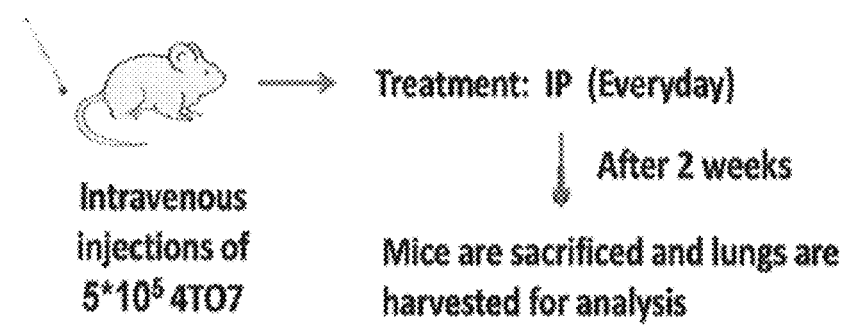
FIG. 5A is a schematic diagram showing a method for determining the anti-metastatic activity of vacuolin-1 in normal BALBc mice injected with mouse breast carcinoma 4TO7 cells.

To exclude the effects of immunodeficiency (nude mice) on the drug effects, another metastasis tumor model was established by tail vein injection of mouse breast carcinoma 4TO7 into normal BALBc mice followed by daily IP injections of vacuolin-1 (2.5 mg/kg) 24 hour later, as illustrated in FIG. 5A.

Figure 5B:
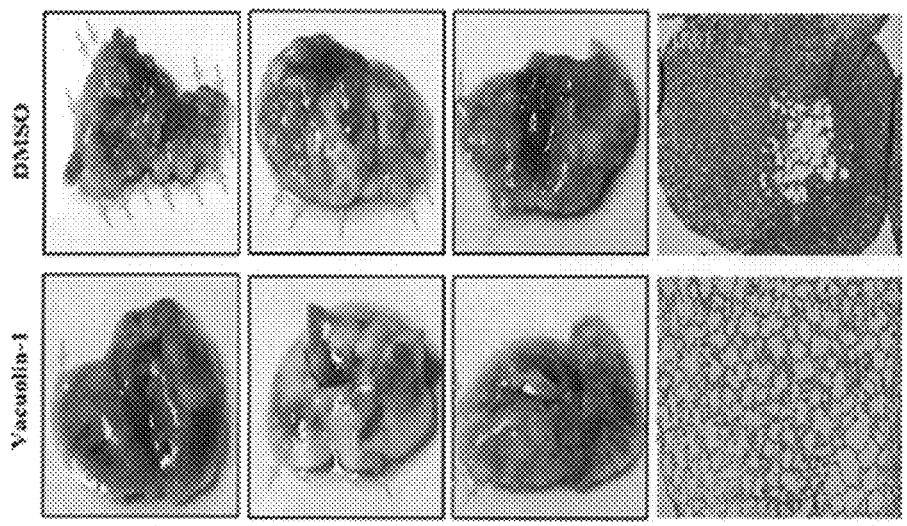
FIG. 5B shows the excised lungs and microscopic images of lungs of mice in control group and treatment group treated with 2.5 mg/kg vacuolin-1.
Figure 5C:
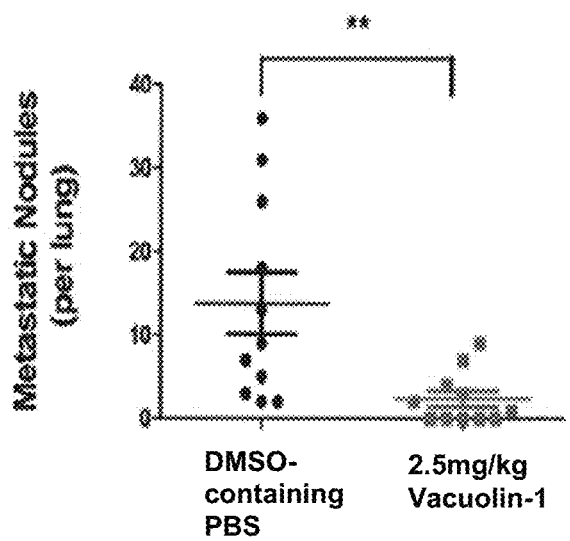
FIG. 5C is a plot showing the number of metastatic nodules counted in mice of treatment group and control group.

As shown in FIG. 5B, 4TO7 cells exhibited much stronger metastastic ability than human LCSCs. Vacuolin-1 treatment showed striking anti-metastatic effects on 4TO7 cells in wild type mice, as shown by the far less tumor nodules in lungs and normal lung histology as compared to the control groups.

Figures 6A, 6B:
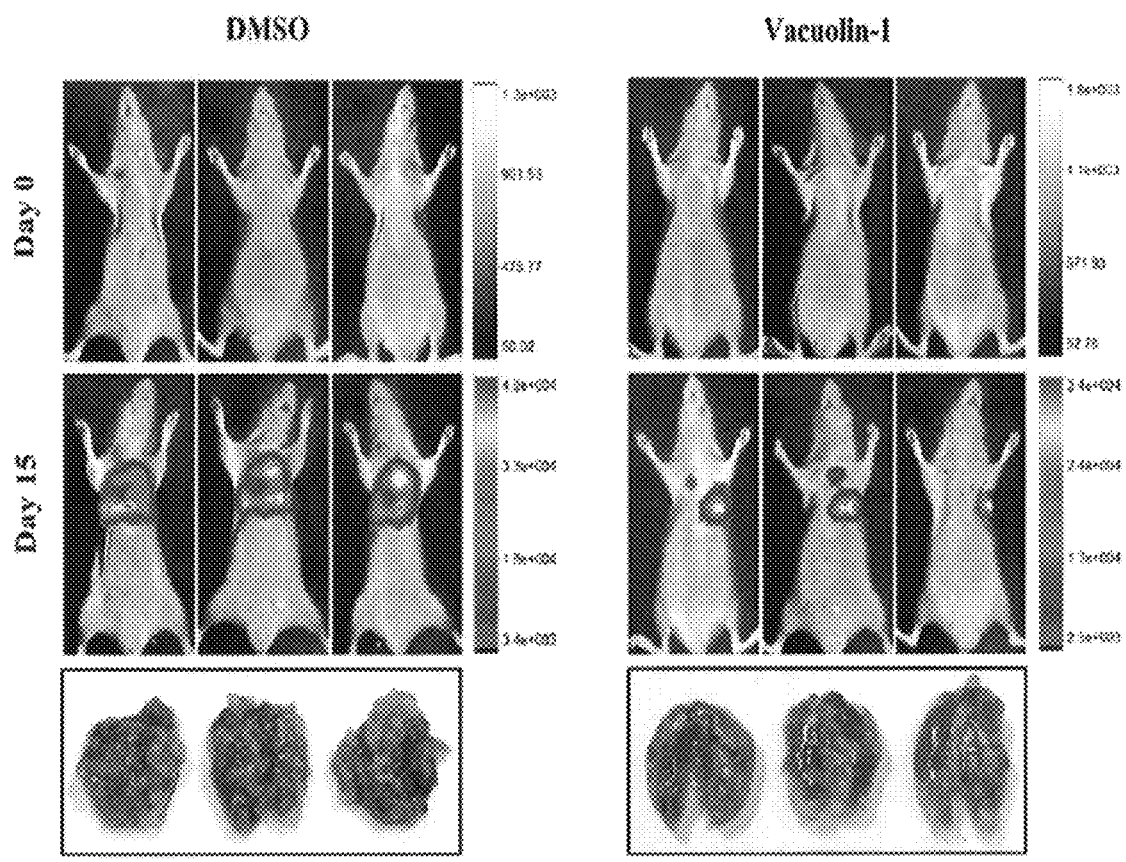
FIG. 6A is a schematic diagram showing a method for determining the anti-metastatic of vacuolin-1 in normal mice injected with Fluc-mCherry-expressing 4TO7 cells.
FIG. 6B shows the images of mice in control group and treatment group treated with 2.5 mg/kg vacuolin-1.

Since 4TO7 cells are more metastatic than LCSCs, Fluc-mCherry-expressing 4TO7 cells were injected into normal mice via tail vein injection followed by IP injections of vacuolin-1 (2.5 mg/kg) 24 hour later, as illustrated in FIG. 6A. The mice were imaged by the Cri Maestro 2 weekly to assess the tumor progression. Mice were sacrificed after 2 weeks, and the number of tumor colonies in lung was counted. As shown in FIG. 6B, vacuolin-1 markedly inhibited metastasis of 4TO7 cells in normal mice.

Figure 7A:
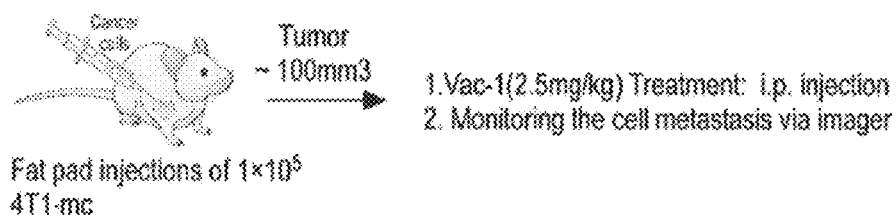
FIG. 7A is a schematic diagram showing a method for determining the anti-metastatic of vacuolin-1 in normal female mice injected with Fluc-mCherry-expressing 4TO7 cells in the fat pad.
Figure 7B:
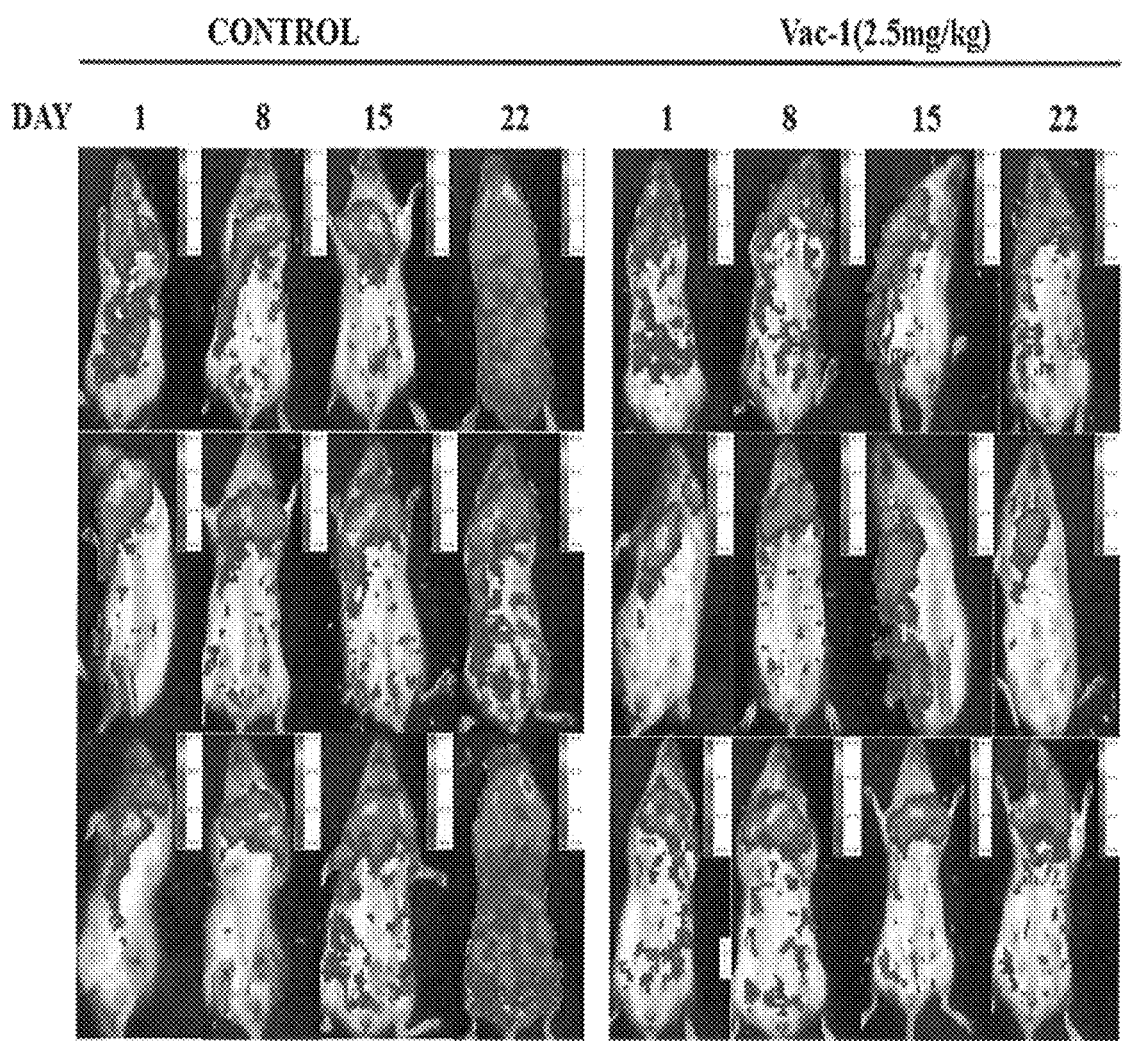
FIG. 7B shows the images of mice in control group and treatment group treated with 2.5 mg/kg vacuolin-1.

The anti-metastasis effects of vacuolin-1 in another metastasis model have also been evaluated. With reference to FIG. 7A, Fluc-mCherry-expressing 4TO7 cells were injected into the fat pad of normal female mice followed by IP injections of vacuolin-1 (2.5 mg/kg) 24 hour later. The mice were imaged by the Cri Maestro 2 weekly to assess the tumor progression. Mice were sacrificed after 4 weeks, and the number of tumor colonies in lung was counted. As shown in FIG. 7B, vacuolin-1 markedly inhibited the metastasis of 4TO7 cells in normal mice.

Example 5

Determination of Toxicity of Vacuolin-1

The inventor found that vacuolin-1 administered at 250 mg/kg via intraperitoneal route had no acute toxicity. Therefore, a test on determining whether vacuolin-1 has acute toxicity via oral route was conducted by administering vacuolin-1 to mice orally.

In particular, vacuolin-1 was administered at a single dose of 250 mg/kg to young adult male and female mice via oral route, and DMSO-containing PBS was administered to another set of male and female mice via oral route as a control group. All animals were observed for 2 weeks after dosing so as to observe mortality and signs of toxicity. During the 2 weeks, the body weight was also measured. After the 2 weeks, organs were excised for histopathology evaluation.

Figure 8A:
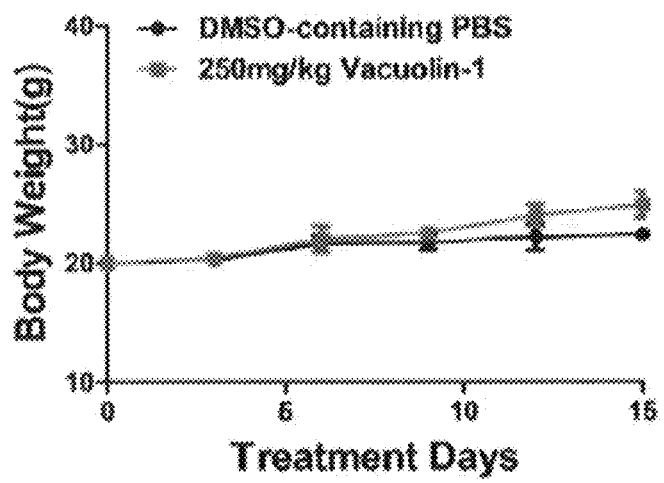
FIG. 8A is a plot showing the body weight of mice in control group and treatment group treated with 250 mg/kg vacuolin-1 in 2 weeks of an acute toxicity evaluation of vacuolin-1.
Figure 8B:
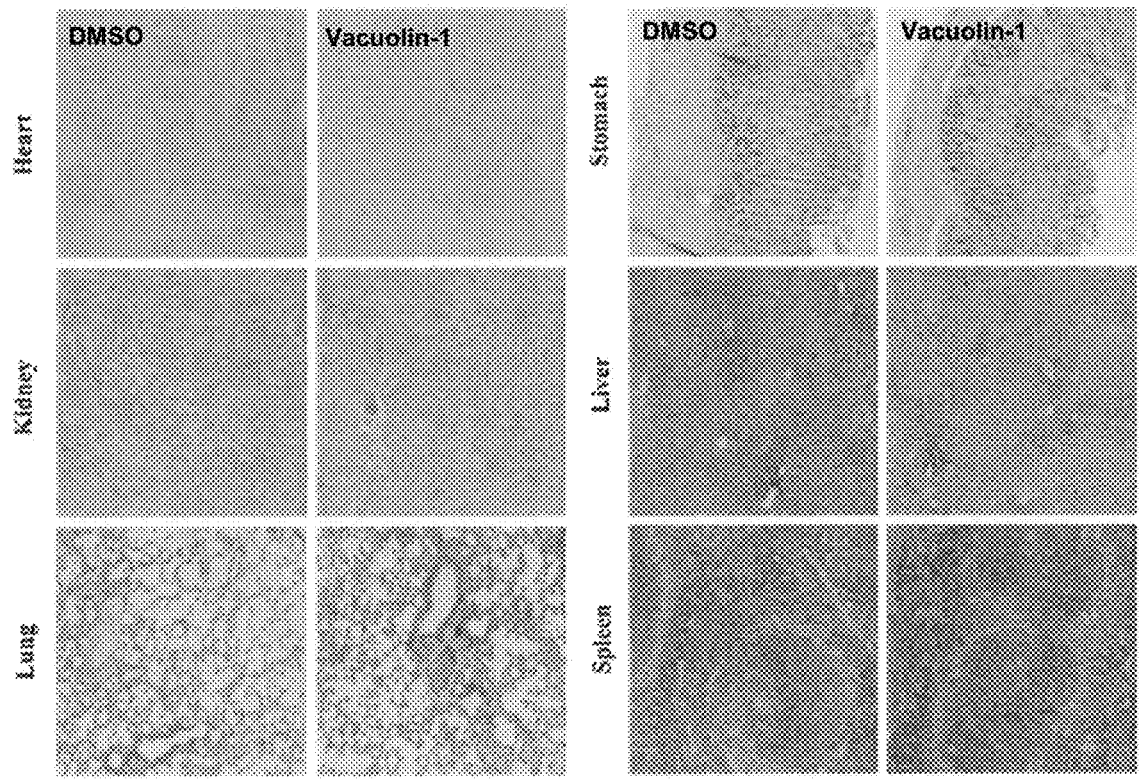
FIG. 8B shows microscopic histological images of different organs of the mice after treatment.

Necropsies were conducted on all test animals and lungs, spleen, liver and kidneys were observed for evidence of drug toxicity. As shown in FIG. 8A, vacuolin-1 (250 mg/kg) has no effects on mouse weight gain, and the treated mice showed no signs of behavior abnormality (data not shown). Referring to FIG. 8B, all tissues or organs in vacuolin-1 treated mice were normal in histological point of view as compared to control groups. Based on these results, it is believed that vacuolin-1 has no acute toxicity in mice.

The sub-acute toxicity of vacuolin-1 was also tested in mice. In particular, 10 mg/kg vacuolin-1 was administered daily to young adult male and female mice via intraperitoneal route for 2 weeks, and DMSO-containing PBS was administered to another set of male and female mice as a control group. All animals were observed for general behavior and signs of abnormality for 2 weeks. During the 2 weeks, the body weight was measured every two days. After the 2 weeks, organs were excised for histopathology evaluation.

Figure 9A:
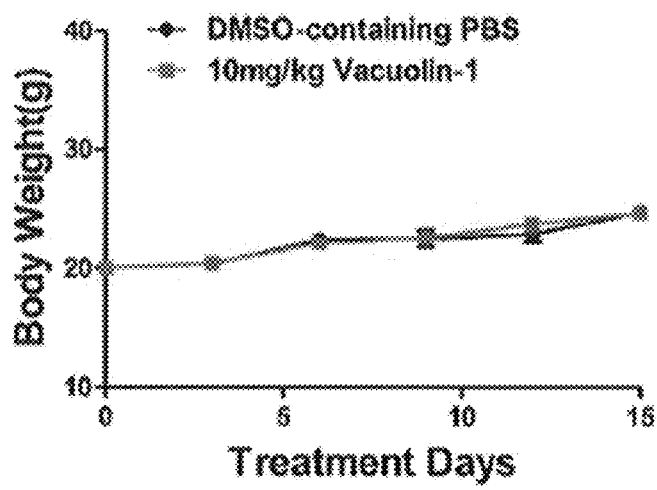
FIG. 9A is a plot showing the body weight of mice in control group and treatment group treated with 10 mg/kg vacuolin-1 in 2 weeks of a sub-acute toxicity evaluation of vacuolin-1.
Figure 9B:
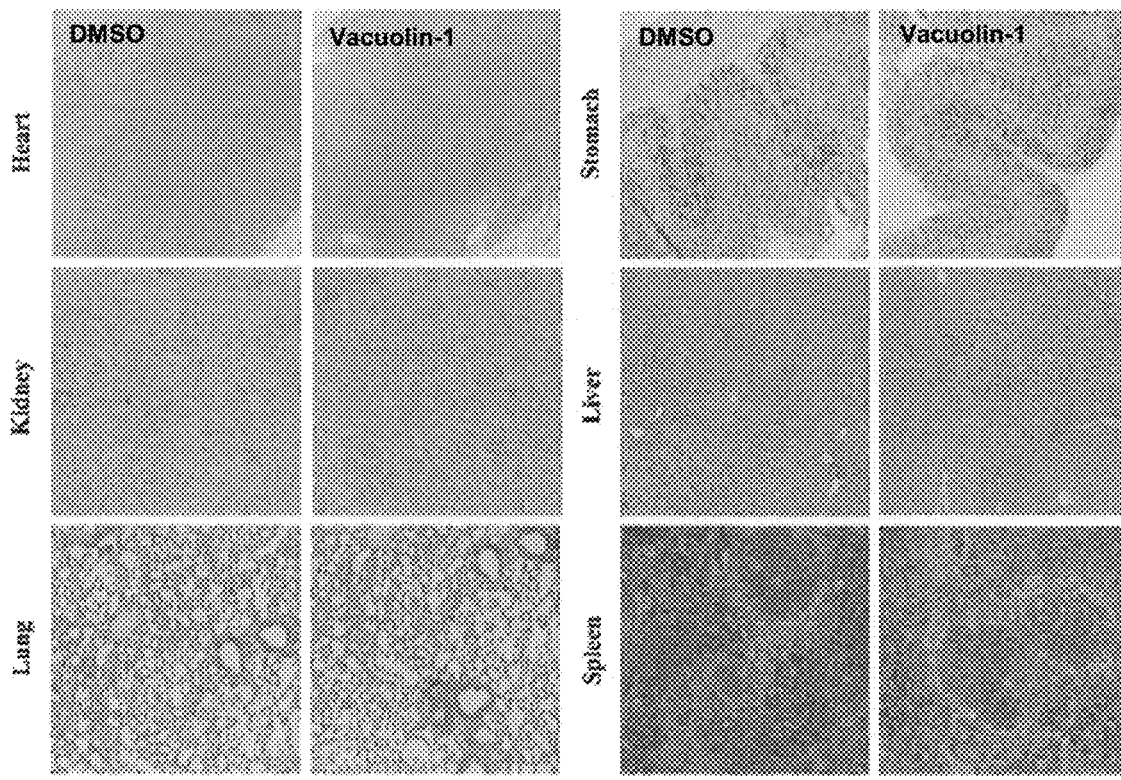
FIG. 9B shows microscopic histological images of different organs of the mice after treatment.

As shown in FIG. 9A, vacuolin-1 (10 mg/kg) has no effects on mouse weight gain, and the treated mice showed no signs of behavior abnormality (data not shown). Likewise, all tissues or organs in vacuolin-1 treated mice were normal compared to the control group, as shown in FIG. 9B. These results show that vacuolin-1 has no sub-acute toxicity in mice.

As for the sub-chronic toxicity of vacuolin-1, 5 mg/kg vacuolin-1 was administered daily to young adult male and female mice via intraperitoneal route for 3 months, and DMSO-containing PBS was administered to another set of male and female mice as a control group. The body weight of the mice was determined every week. All animals were observed for general behavior and signs of abnormality during the experimental period. After the 3 months, organs were excised for histopathology evaluation.

Figure 10A:
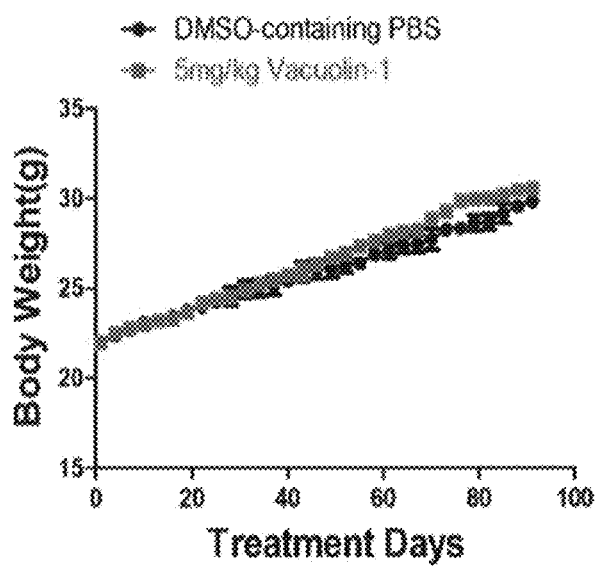
FIG. 10A is a plot showing the body weight of mice in control group and treatment group treated with 5 mg/kg vacuolin-1 in 3 months of a sub-chronic toxicity evaluation of vacuolin-1.
Figure 10B:
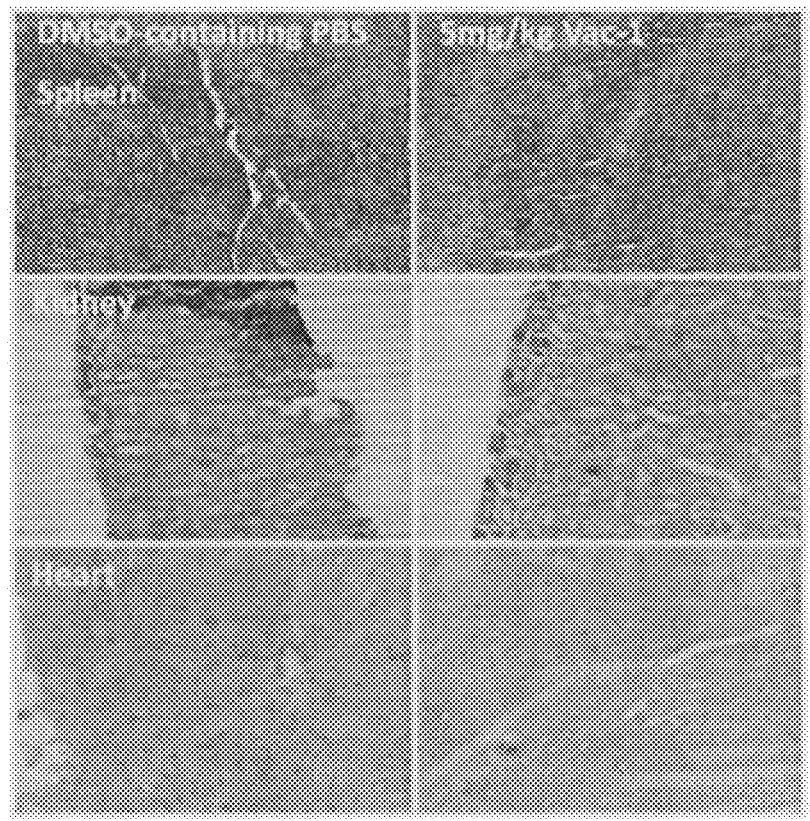
FIG. 10B shows microscopic histological images of different organs of the mice after treatment.

As shown in FIG. 10A, vacuolin-1 (5 mg/kg) has no effect on mouse weight gain, and the treated mice showed no signs of behavioral abnormality (data not shown). Likewise, all tissues or organs in vacuolin-1 treated mice were normal as compared to the control group, as shown in FIG. 10B. Therefore, based on the above results, it is believed that vacuolin-1 has no sub-chronic toxicity in mice.

The invention claimed is:

1. A method of treating a subject suffering from metastatic breast cancer, comprising the step of administering a compound having a structure of Formula I to the subject, Formula I

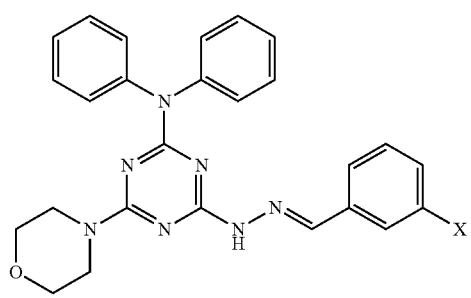

wherein X is a hydrogen, hydroxyl, or halogen, and wherein the compound is administered to the subject at about 2.5 mg/kg via intraperitoneal delivery to suppress the migration or invasion of metastatic breast cancer to lung tissue.

2. The method of claim 1, wherein the compound has a structure of Formula I with X being a halogen.

3. The method of claim 1, wherein the compound has a structure of Formula II,

Formula II

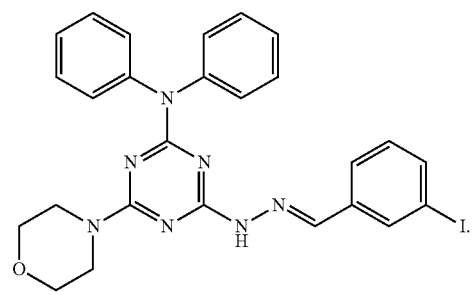

4. The method of claim 1, wherein the compound is administered in combination with one or more chemotherapy drug or immunotherapy drug to the subject.

5. The method of claim 4, wherein the chemotherapy drug is selected from the group consisting of taxol, 5-Fu, and temirolimus, and the immunotherapy drug is PD-1 or a PD-L1 inhibitor.

* * * * *